United States Patent
Ariav

(10) Patent No.: US 7,266,989 B2
(45) Date of Patent: Sep. 11, 2007

(54) SENSOR SYSTEM FOR HIGH-PRECISION MEASUREMENTS OF TEMPERATURE, COMPOSITION, AND/OR PRESSURE OF A FLUID

(75) Inventor: Arie Ariav, Doar-Na Hof Ashkelon (IL)

(73) Assignee: Nexense Ltd., Yavne (IL)

( * ) Notice: Subject to any disclaimer, the term of this patent is extended or adjusted under 35 U.S.C. 154(b) by 11 days.

(21) Appl. No.: 11/125,222

(22) Filed: May 10, 2005

(65) Prior Publication Data

US 2005/0252294 A1   Nov. 17, 2005

(30) Foreign Application Priority Data

May 11, 2004   (IL) .................................. 161937

(51) Int. Cl.
*G01N 29/024*   (2006.01)
*G01N 29/30*   (2006.01)
*G01K 11/24*   (2006.01)

(52) U.S. Cl. ........................ 73/24.01; 374/119
(58) Field of Classification Search ............... 73/24.01; 374/119
See application file for complete search history.

(56) References Cited

U.S. PATENT DOCUMENTS

| 4,235,099 | A | * | 11/1980 | Ishizaka ..................... 73/32 A |
| 4,255,964 | A | * | 3/1981 | Morison .................... 73/24.01 |
| 5,181,778 | A | * | 1/1993 | Beller ......................... 374/119 |
| 5,581,014 | A | * | 12/1996 | Douglas .................... 73/24.01 |
| 6,157,894 | A | * | 12/2000 | Hess et al. ..................... 702/54 |
| 6,681,635 | B1 | * | 1/2004 | Van Schaik ................. 73/597 |
| 6,820,462 | B2 | * | 11/2004 | Cardelius ................... 73/24.01 |

* cited by examiner

*Primary Examiner*—Hezron Williams
*Assistant Examiner*—Rose M Miller

(57) ABSTRACT

A sensor system immersible in an ambient-fluid for sensing at least two conditions of the ambient fluid, includes a sealed chamber filled with a reference fluid of a known composition and/or pressure, and two acoustic transmission channels, one including the reference fluid, and the other including the ambient fluid. Measuring circuitry measures (a) the transit time of an energy wave through one transmission channel to determine the temperature of the fluid within the sealed chamber and thereby the temperature of the ambient fluid; and (b) the transit time of an energy wave through the other transmission channel to determine the composition and/or the pressure of the ambient fluid.

19 Claims, 3 Drawing Sheets

SENSOR SYSTEM FOR HIGH-PRECISION MEASUREMENTS OF TEMPERATURE, COMPOSITION, AND/OR PRESSURE OF A FLUID

RELATED PATENT APPLICATION

This application claims the benefit of priority of Israel patent application No. 161937, filed on May 11, 2004.

FIELD AND BACKGROUND OF THE INVENTION

The present invention relates to a sensor system for making high-precision measurements of temperature, composition, and/or pressure of a fluid. The invention is particularly useful for making such high precision measurements of an ambient gas, such as present in a processing chamber for processing semiconductor elements, and also for making such measurements in an ambient liquid, such as in a swimming-pool or other body of water. The invention is therefore described below particularly with respect to the above applications, but it will be appreciated that the invention is useful in many other applications.

The measurement of the temperature, composition, and/or pressure of gases present in processing chambers during the processing of semiconductor wafers or other elements is of critical importance to such processing operations. Various measuring instruments have been used for this purpose, but such measuring instruments generally suffer from one or more of the following drawbacks: high initial and maintenance costs; the need for frequent re-calibration; insufficiently high precision; and/or relatively large bulk, which may interfere with the processing operations, disturb the temperature distribution, and/or hinder the handling of the workpieces.

Similar problems are involved in measuring the temperature and/or composition of a liquid, or of a chemical characteristic of the liquid. For example, it is frequently necessary to measure the composition of a body of water, e.g., the chlorine content or pH of a swimming pool. Instruments presently available for making this type of measurement are generally expensive, imprecise, and/or not convenient to use.

OBJECTS AND BRIEF SUMMARY OF THE PRESENT INVENTION

An object of the present invention is to provide a sensor system having advantages in one or more of the above respects for making high-precision measurements of temperature, composition, and/or pressure of a fluid.

According to a broad aspect of the present invention, there is provided a sensor system immersible in an ambient fluid for sensing at least two conditions of the ambient fluid, comprising: a sealed chamber filled with a reference fluid of a known composition and/or pressure; a first energy wave transmission channel defined by a first transmitter at one end of the transmission channel, a first receiver at the opposite end of the transmission channel, and the reference fluid inbetween; a second energy wave transmission channel defined by a second transmitter at one end, a second receiver at the opposite end, and the ambient fluid inbetween; and measuring circuitry for measuring (a). the transit time of an energy wave through the first transmission channel, and for utilizing the latter measurement to determine the temperature of the fluid within the sealed chamber, and thereby the temperature of the ambient fluid in which the sensor system is immersed; and (b) the transit time of an energy wave through the second transmission channel, and for utilizing the latter measurement to determine the composition and/or the pressure of the ambient fluid in which the sensor system is immersed.

The measuring circuitry used is preferably that described in U.S. Pat. No. 6,621,278, assigned to the assignee of the present application, the contents of which patent are incorporated herein by reference.

According to further features in the preferred embodiments of the invention described below, the first and second energy wave transmission channels are carried by a common housing to be enveloped by the ambient fluid.

According to still further features in the described preferred embodiments, the sensor system further comprises: a second sealed chamber filled with a second reference fluid of a known composition and/or pressure; the second sealed chamber including a third transmitter and a third receiver defining a third energy wave transmission channel with the second reference fluid therein; the measuring circuitry also measuring: (c) the transit time of an energy wave through the third energy wave transmission channel and utilizing the latter measurement to determine the composition and/or the pressure of the ambient fluid.

In the described preferred embodiments, the first mentioned sealed chamber is defined by rigid walls such that measuring the transit time of an energy wave through the first energy wave transmission channel enables the sensor system to determine the temperature and composition of the ambient fluid; and the second sealed chamber is defined by at least one wall which is pressure-deformable, the reference fluid within the second sealed chamber being initially of a known pressure such that measuring the transit time of an energy wave through the third energy wave transmission channel also enables the sensor system to determine the pressure of the ambient fluid.

In one described preferred embodiment, the first and second reference fluids are gases of known composition, such as those used in a processing chamber for processing semiconductor elements. In such an application, the sensor assembly is capable of continuously monitoring the temperature, pressure and composition of the gases in the processing chamber.

In another described preferred embodiment, the reference fluids are liquids, such as water of known composition and/or pH, whereby the sensor assembly is capable of measuring the temperature, pressure (e.g., depth) and chemical composition (e.g., pH value) of a liquid, such as the water in a swimming pool.

In all the described preferred embodiments, the energy wave is a sonic wave, although the invention could be implemented with electromagnetic waves, or modulated waves, as described for example in the above-cited U.S. Pat. No. 6,621,278, incorporated herein by reference.

Further features and advantages of the invention will be apparent from the description below.

BRIEF DESCRIPTION OF THE DRAWINGS

The invention is herein described, by way of example only, with reference to the accompanying drawings, wherein.

Figure 1:
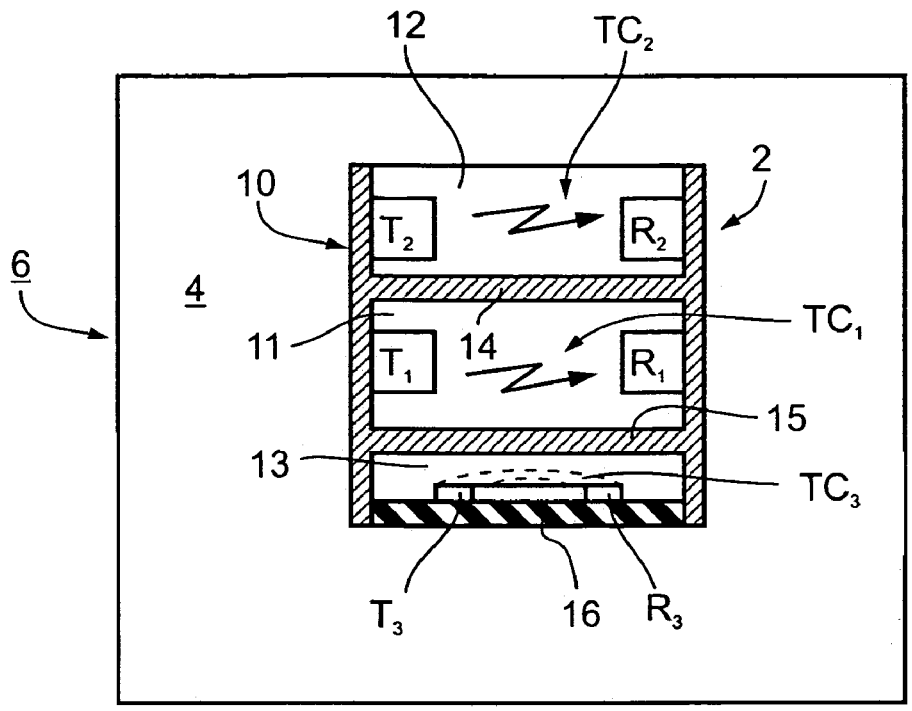
FIG. 1 illustrates one, sensor system constructed in accordance with the present invention for sensing temperature, composition, and/or pressure of an ambient fluid in which the sensor system is immersed.

It is to be understood that the foregoing drawings, and the description below, are provided primarily for purposes of facilitating understanding the conceptual aspects of the invention and various possible embodiments thereof, including what is presently considered to be a preferred embodiment. In the interest of clarity and brevity, no attempt is made to provide more details than necessary to enable one skilled in the art, using routine skill and design, to understand and practice the described invention. It is to be further understood that the embodiments described are for purposes of example only, and that the invention is capable of being embodied in other forms and applications than described herein.

DESCRIPTION OF PREFERRED EMBODIMENTS

The sensor system illustrated, in the drawings is designed for sensing at least two conditions of an ambient fluid in which the sensor system is immersed. The ambient fluid may be a gas, such as a gaseous atmosphere in a processing chamber for processing articles, e.g., semiconductor elements; in such case, the sensor system would sense the temperature, composition, and/or pressure of the gaseous atmosphere. The ambient fluid may also be a liquid, such as the water in a swimming pool, in which case the sensor system would sense the temperature and composition, e.g., chlorine content or pH of the water. Such a sensor system may also be used for measuring the pressure of the liquid, e.g., the depth at which the sensor system is immersed in a body of water or other liquid.

The sensor system illustrated in FIG. 1 is therein generally designated 2. As shown, it is immersed in a fluid 4 within a container, generally designated 6. In a processing-chamber type implementation of the invention, container 6 would be a closed processing chamber, and fluid would be a gaseous mixture whose temperature, composition, and/or pressure is to be continuously monitored. In a swimming-pool type implementation of the invention, containers would be a swimming-pool containing water whose temperature and composition (e.g., pH or chlorine content) are to be measured or continuously monitored.

Sensor system 2 includes a common housing, generally designated 10, which houses an assembly of a plurality of sensors each for sensing a predetermined condition of the ambient fluid 4 in which the sensor assembly is immersed. Thus, housing 10 defines: a first sealed chamber 11 containing a first reference fluid; a space 12 to be exposed to the ambient fluid 4 in which the sensor assembly is immersed; and a second sealed chamber 13 containing a second reference fluid. All the walls 14, 15 of housing 10 defining the two sealed chambers 11, 13 and the exposed space 12 are rigid, except that sealed chamber 13 includes one wall 16 which is deformable in response to the differential pressure between the interior of its sealed chamber 13 and the ambient fluid 4.

Each of the two chambers 11, 13 and space 12 includes a sensor of the type described in the above-cited U.S. Pat. No. 6,621,278. As described in that patent, such sensors are capable of measuring, with a high degree of precision, virtually any condition influencing the transit time of an energy wave through a transmission channel defined by a transmitter at one end, and a receiver at the opposite end. Thus, measurement of the transit time of an energy wave from the transmitter to the receiver in the respective transmission channel enables a precise measurement of the condition influencing such transit time. In the sensor assembly illustrated in FIG. 1, the energy wave whose transit time is measured is a sonic wave.

Thus, sealed chamber 11 is filled with a reference fluid of a known composition and pressure, e.g., the desired composition and pressure of the ambient fluid 4 in which the sensor assembly 2 is immersed. Sealed chamber 11 includes a transmitter $T_1$ at one end and a receiver $R_1$ at the opposite end to define therebetween a transmission channel $TC_1$ which includes the reference fluid within chamber 11.

Space 12, which is exposed to the ambient fluid 4 when immersed therein, includes a second transmitter $T_2$ at one end, and a second receiver $R_2$ at the opposite end, to define therebetween a second transmission channel $TC_2$ with the ambient fluid 4 in which the sensor assembly is immersed.

Sealed chamber 13, on the opposite side of sealed chamber 11 from the exposed space 12, is also filled with a reference fluid of known composition, such as the desired composition of the ambient fluid 4 in which the sensor assembly is immersed. In addition, the pressure of reference fluid within sealed chamber 13 is also initially known.

As indicated above, the walls 14, 15 defining sealed chamber 11 are rigid; therefore, the reference fluid therein, defining transmission channel $TC_1$ with transmitter $T_1$ and receiver $R_1$, remains of the same pressure and composition even when immersed within the ambient fluid 4. Accordingly, transmission channel $TC_1$ of sealed chamber 11 will be sensitive to the temperature of the ambient fluid 4 in which it is immersed.

On the other hand, transmission channel $TC_2$, defined by transmitter $T_2$ and receiver $R_2$ exposed to the ambient fluid 4 in which the sensor assembly 2 is immersed, includes such ambient fluid in its transmission channel; therefore transmission channel $TC_2$ will be sensitive not only to the temperature, but also to the pressure and composition, of the ambient fluid 4.

The walls of sealed chamber 13 are also rigid except for one wall, wall 16, which is in the form of a pressure-deformable membrane. Transmission channel $TC_3$ within chamber 13 is defined by an elastomeric strip 17 bonded to membrane 16 between transmitter $T_3$ and receiver $R_3$, so as to be deformable with membrane 16 in accordance with the pressure of the ambient fluid 4 in which the sensor assembly is immersed, therefore, transmission channel $TC_3$ will be sensitive to the pressure of the ambient fluid.

Figure 2:
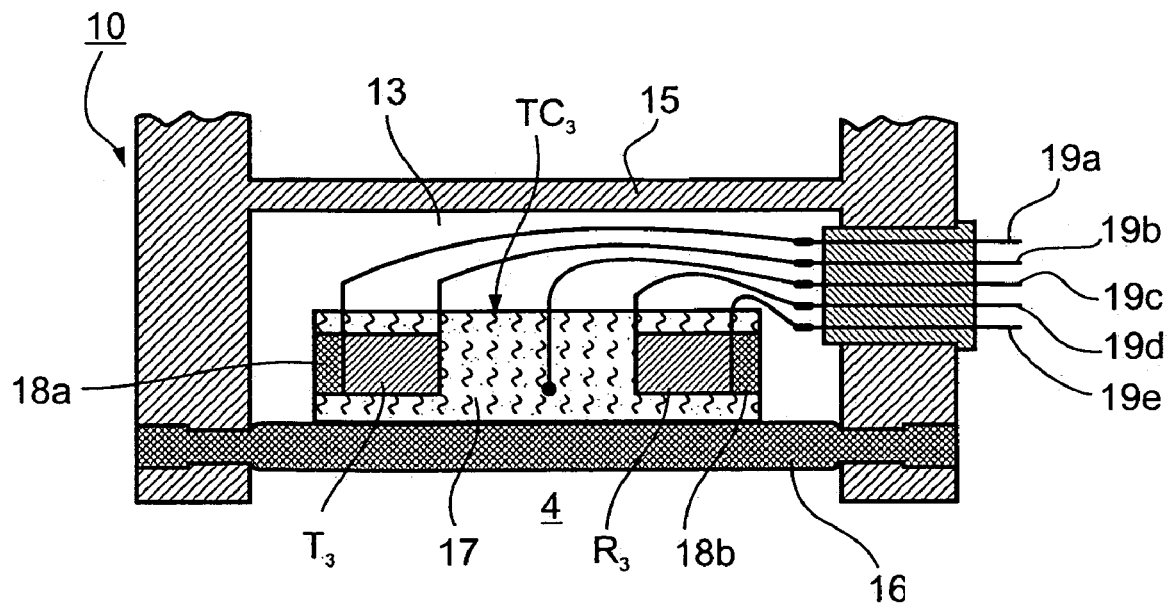
FIG. 2 more particularly illustrates the construction of one of the sealed chambers in the sensor system of FIG. 1, namely the one including a pressure-displaceable wall for use in measuring the pressure of the ambient fluid.

FIG. 2 more particularly illustrates a preferred construction of the pressure-deformable wall 16 including the elastomeric strip 17 defining transmission channel $TC_3$ with transmitter $T_3$ and receiver $R_3$. Such a construction is described in International Patent Application PCT/IL2004/000138, assigned to the same assignee as the present application and incorporated herein by reference. Elastomeric strip 17 has high transmissivity and low attenuation properties with respect to the sonic waves transmitted there-through from its transmitter $T_3$ to its receiver $R_3$. Preferably, elastomeric strip 17 further includes two absorbent elements 18a, 18b, located on opposite sides of the transmitter $T_3$ and receiver $R_3$, respectively, having high attenuation properties with respect to the sonic waves to thereby dampen or absorb the sonic waves except those in the narrow acoustical channel defined by elastomeric strip 17 between the transmitter and receiver. The various elements of transmission channel ($TC_3$ are electrically connected to the external circuitry: by terminals 19a-19e. Further details of the construction and operation of such a pressure sensor are described in the above-cited International Patent Application.

Figure 3:
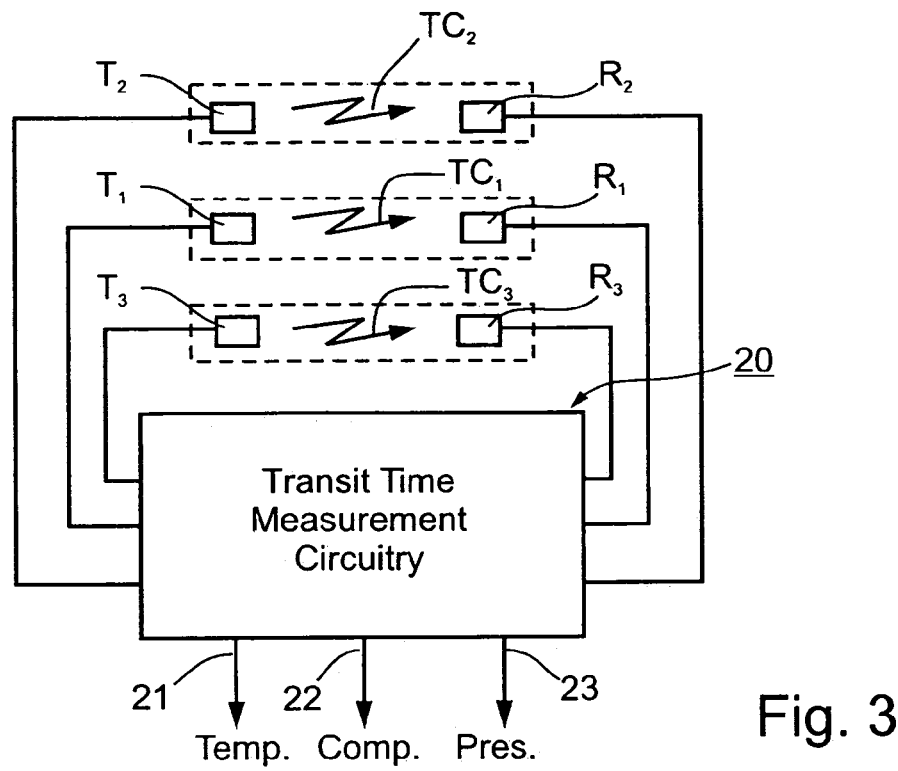
FIG. 3 is a block diagram illustrating the sensor system of FIG. 1 and the measuring circuitry for measuring the transit time of energy waves through the various transmission channels defined by the sensor system.

FIG. 3 is a block diagram illustrating the three transmission channels $TC_1$, $TC_2$ and $TC_3$ defined by sensor assembly 2, and the measuring circuitry, generally designated 20, for measuring the transit time of an energy wave through each of the three transmission channels, in order to measure the condition affecting the transit time of a sonic wave through the respective channel. Measuring circuitry 20 illustrated in FIG. 3 is preferably one which, for each transmission channel $TC_1$-$TC_3$: (a) transmits a cyclically-repeating energy wave through the transmission channel from its transmitter to its receiver; (b) continuously changes the frequency of the transmitter according to changes in the monitored condition while maintaining the number of waves in the transmission channel as a whole integer; and (c) utilizes the changes in frequency of the transmitter to provide a continuous indication of the instantaneous transit time of the energy wave through the transmission channel, and thereby a continuous indication of the monitored condition. As indicated above, the energy wave is preferably a sonic wave and the conditions monitored by the three transmission channels in this case are temperature, composition and pressure, appearing at the outputs 21, 22 and 23, respectively.

Figure 4:
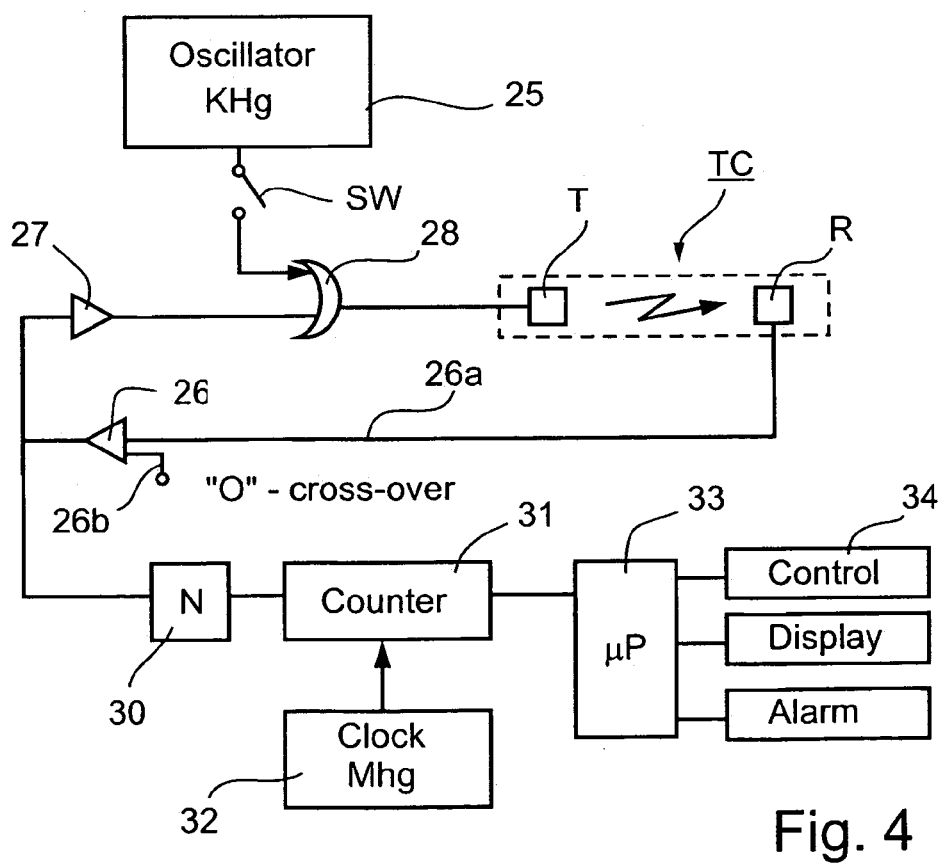
FIG. 4 more particularly illustrates the measuring circuit of each sensor in the sensor system of FIG. 1.

FIG. 4 illustrates a preferred measuring circuit which may be used for each of the transmission channels $TC_1$-$TC_3$ as described in the above-cited U.S. Pat. No. 6,621,278, incorporate herein by reference. In FIG. 4, the respective transmission channel is identified as TC and the respective transmitter and receiver are identified as T and R.

Initially, oscillator 25 is energized while switch SW is closed so as to cause transmitter T to transmit a succession of sonic pulses until such pulses are received by receiver R. Once the pulses are received by receiver R, switch SW is opened so that the pulses received by the receiver are thereafter used for controlling the transmitter T.

The sonic signals received by receiver R are fed to a comparator 26 via its input 26a. Comparator 26 includes a second input 26b connected to a predetermined bias so as to detect a predetermined fiducial in the received signal. In the example illustrated in FIG. 4, this predetermined fiducial point is the "zero" cross-over point of the received signal; therefore, input 26b of comparator 26 is at a zero bias.

The output of comparator 26 is fed to an amplifier 27, which is triggered to produce an output signal at each fiducial point (zero cross-over point) in the signals received by receiver R. The outputs from amplifier 27 are fed via an OR-gate 28 to trigger the transmitter T for the next sonic pulse. Since switch SW is open, transmitter T will thus be triggered by each signal received by the receiver R to transmit the next sonic pulse in the succession of pulses.

It will thus be seen that the frequency of the output pulses or signals from transmitter T will change with a change in the transit velocity of the energy wave in the respective transmission channel, or in the transit distance, i.e., the spacing between the transmitter T and receiver R, in the respective transmission channel. It will also be seen that the number of wavelengths or pulses in the signal transmitted by the transmitter T and received by receiver R will be a whole integer. This change in frequency by the transmitter, while maintaining the number of waves between the transmitter and receiver as a whole integer, enables a precise determination to be made of the transit time of the energy wave in the respective channel.

A summing circuitry, including counters 30 and 31, clock 32 and microprocessor 33, enables the detected frequency difference, and thereby the measurement precision, to be increased by a factor "N", such that the precision of the measurement can be preset, almost without limitation, by the selection of the appropriate frequency, clock rate for clock 32, and summation factor "N" for counter 30. As further shown in FIG. 4, the output from microprocessor 33 may be used for display, alarm and/or control purposes, as schematically shown at 34.

Further details of the construction and operation of such a system for measuring the transit time of an energy wave through a transmissive channel are available from the above-cited International Applications and U.S. Pat. No. 6,621,278, incorporated herein by reference.

The sensor system described above may be used in the following manner for measuring the temperature, pressure and/or composition of an ambient fluid in which the sensor assembly shown in FIG. 1 is immersed. As indicated earlier the ambient fluid 4 may be a gas, such as the gaseous atmosphere in a processing chamber for processing semiconductor elements, in which case the sensor system precisely monitors the temperature, composition and pressure of the gaseous mixture within the processing chamber. Alternatively, the ambient fluid 4 could be a liquid, such as water in a swimming pool or the like, for closely monitoring the temperature and/or the composition (e.g., pH or chlorine content) of the water. The sensor system could also be used, in such application, for measuring the pressure of the liquid, (e.g., the depth in which the sensor assembly is immersed) for providing a depth measurement or for compensating the temperature or composition measurement by the depth at which the sensor assembly is immersed.

When the sensor assembly is used for monitoring one of the above conditions of a gaseous mixture in a processing chamber, the reference fluid within chambers 11 and 13 would preferably be a gaseous mixture of the desired concentration and pressure. Thus, when the transit time of the energy wave through transmission channel $TC_1$ is measured, this would provide an indication of the temperature of the ambient fluid (gaseous mixture) since the reference fluid within chamber 11 is brought to the same temperature as the ambient fluid in which the sensor assembly is immersed.

On the other hand, since space 12 carrying transmitter $T_2$ and receiver $R_2$, defining transmission channel $TC_2$, is exposed to the ambient fluid 4 in which the sensor assembly 2 is immersed, the transit time of the energy wave through transmission channel $TC_2$ would be influenced by the composition of the ambient fluid, and therefore could be used for providing a measurement of the ambient fluid composition.

In addition, since sealed chamber 13, containing the pressure-deformable wall 16, deforms in accordance with the pressure of the ambient fluid in which the sensor assembly 2 is immersed, elastomeric strip 17, defining transmission channel $TC_3$ with the transmitter $T_3$ and receiver $R_3$, will vary length according to the deformation of wall 16, and thereby according to the pressure of the ambient fluid. The transit time of the energy wave through transmission channel $TC_3$ will therefore vary with the pressure of the ambient fluid 4; accordingly, the measurement of this transit time will provide a measurement of the pressure of the ambient fluid.

Figure 5:
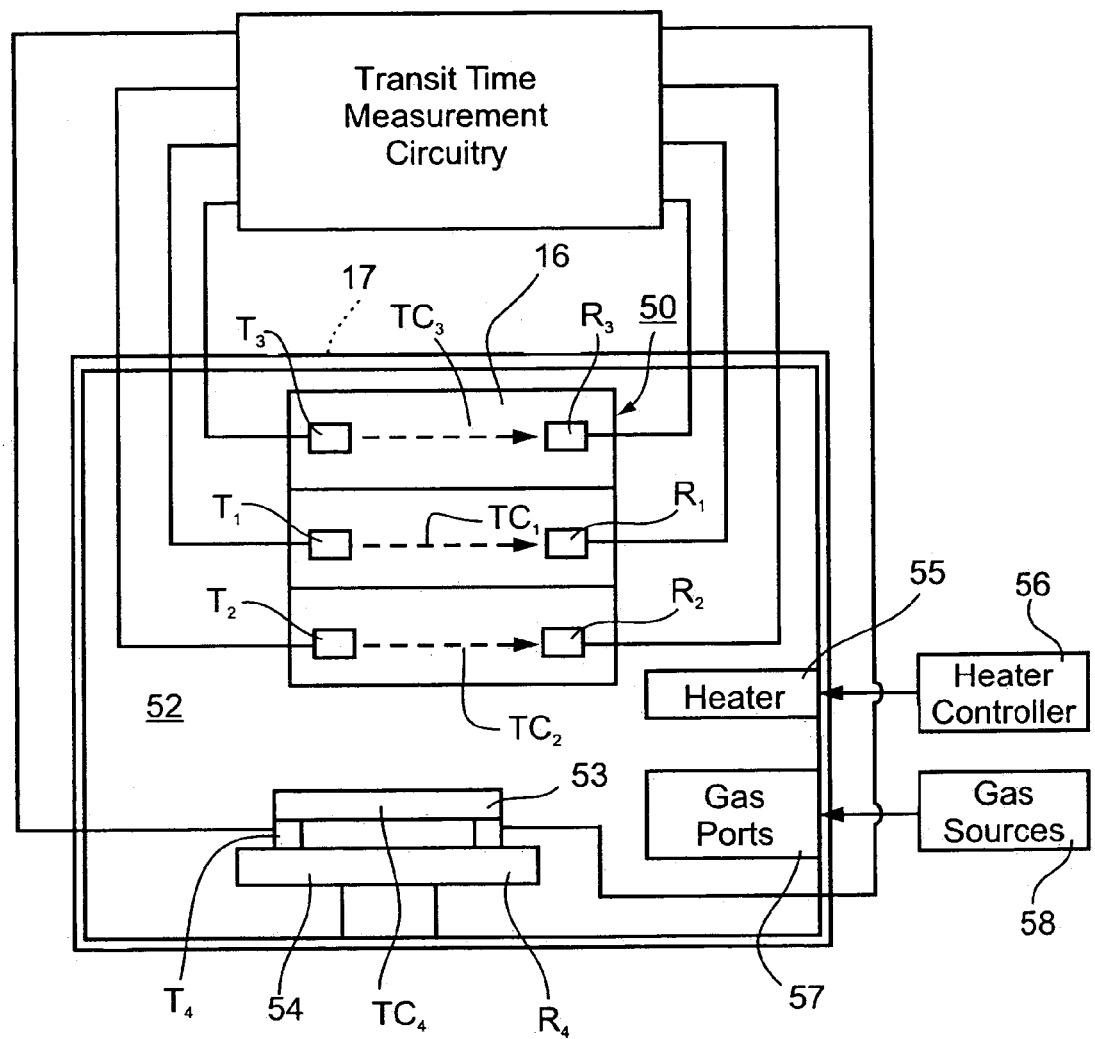
FIG. 5 illustrates a processing chamber for processing workpieces including a sensor system in accordance with the present invention.

FIG. 5 illustrates a sensor assembly, generally designated 50, built into the wall of a processing chamber 52 for processing work pieces 53, such as semiconductor elements, supported on a table 54. Processing chamber 52 includes an electrical heater 55 controlled by controller 56 for producing a desired temperature within the processing chamber 52. The processing chamber further includes ports 57 communicating with a plurality of sources of gases 58 for introducing a mixture of gases of the desired composition and pressure into the processing chamber according to the processing operation to be performed with respect to the workpiece 53.

Sensor assembly 50 may be integrally formed in one of the walls of the processing chamber 52, preferably at a location as close as possible to that to be occupied by the workpiece 53. In FIG. 5, the top wall of the processing chamber 52 is integrally formed with the housing 10 (FIG. 1) of the sensor assembly 50 so as to define the two sealed chamber 11, 13 to contain the two reference fluids of known composition and pressure, and the space 12 to be exposed to the gaseous mixture within the processing chamber. Thus, chamber 11 includes the transmitter $T_1$ and receiver $R_1$ defining the first transmission channel $TC_1$ with the reference fluid in that chamber; space 12 includes the transmitter $T_2$ and receiver $R_2$ which defines the transmission channel $TC_2$ with the gaseous mixture within the processing chamber; and chamber 13 includes the elastomeric strip 17 and the transmitter $T_3$ and receiver $R_3$ of transmission channel $TC_3$.

As described above, all the walls defining processing chamber 11 and space 12 are rigid, so that the transit distances of the two transmission channels $TC_1$ and $TC_2$ remain constant; accordingly, transmission channel $TC_1$ will be influenced by, and therefore provide a measurement of, the temperature of the reference fluid within sealed chamber 11. On the other hand, transmission channel $TC_2$ will be influenced by, and will therefore provide a measurement of, the composition of the gaseous mixture within the processing chamber.

As further described above, strip 17 of elastomeric material defining transmission channel $TC_3$ is carried by pressure-deformable wall 16 of chamber 13 so that the transit distance of transmission channel $TC_3$ will be changed according to the pressure within the processing chamber 52 as sensed by wall 16. Accordingly, transmission channel $TC_3$, will change in length in accordance with the pressure within the processing chamber, such that measuring the transit time of the energy wave through transmission channel $TC_3$ will provide a measurement of the pressure within the processing chamber.

The system illustrated in FIG. 5 further, includes the transit time measuring circuitry 20 of FIG. 4 for measuring the transit time of an energy wave through each of the three transmission channels $TC_1$-$TC_3$, thereby producing an output 21 corresponding to the measured temperature, an output 22 corresponding to the measured composition, and an output 23 corresponding to the measured pressure. The temperature measurement output 21 may be merely displayed, or may be applied to the heater controller 56 for controlling the electrical heater 55; and the composition and pressure outputs 22 and 23 may also be merely displayed, or may be applied to the gaseous mixture source 58 to control the composition, as well as the pressure, of the gas mixture introduced via inlets 57 into the processing chamber.

It will thus be seen that, in order to control the temperature, pressure and composition of processing chamber 52, it is only necessary to introduce into the two sealed chambers 11 and 13 reference gases of the desired composition and pressure according to the particular processing operation to be performed, whereupon the sensor assembly 50 will automatically control (or merely display), as described above, the temperature, pressure and composition of the gases within the processing chamber. This control (or display) will be effected with a minimum interference of the processing operation, a minimum disturbance of the temperature distribution on the workpiece, and a minimum hindering of the handling of the workpiece.

If it is necessary or desirable also to sense the actual temperature of the workpiece, this may be conveniently done in the processing chamber illustrated in FIG. 5 also with a minimum interference of the processing operation, a minimum disturbance of the temperature distribution on the workpiece, and a minimum hindering of the handling of the workpiece. Thus, as shown in FIG. 5, the workpiece 53 is supported at its opposite sides by a pair of supporting elements 59a, 59b, which elements include a fourth transmitter $T_4$ and a fourth receiver $R_4$, respectively, defining a fourth transmission channel $TC_4$ which is through the workpiece itself. Since the temperature of the workpiece affects the transit time of the acoustical wave through the workpiece in a manner which is known, or which can easily be determined, it will be seen that measurement of the transit time through acoustical channel $TC_4$ in the manner described above will enable determination of the precise temperature of the workpiece itself.

The supporting elements 59a, 59b may be, for example, pins, a supporting ring, or the like, commonly used for spacing the workpiece from its supporting table 54. If the temperature of the workpiece is to be particularly high, such as to be damaging to the transmitter or receiver $T_4$, $R_4$, the supporting elements could include a heat-resistant insulator to insulate the transmitter and receiver from the workpiece. Since the transit time of the heat-resistant insulator used also is known or can be easily determined at the respective temperature involved, this known value can be taken into account in determining the transit time of the acoustical wave through the workpiece itself, and thereby the temperature of the workpiece.

While the invention has been described with respect to a preferred construction suitable for a number of applications, it will be appreciated that variations in the construction of the sensor assembly, and that other applications of such a sensor assembly, may be made. For example, the sensor assembly could include only two transmission channels, to sense only two conditions (e.g., temperature and composition), or more than three channels to sense additional condition, e.g., fluid flow velocity. In addition, the pressure-deformable membrane 16 could include a transmission channel, corresponding to its transmission channel $TC_3$, on each of its opposite faces so as to serve as a differential-type pressure sensor, as described in the above-cited International Patent Application.

The three sensor elements defining the three transmission channels $TC_1$, $TC_2$, $TC_3$, could be horizontally aligned, rather than vertically stacked, or could be arranged in any other desired form. In some cases, it may be desirable to enclose transmitter $T_2$ and receiver $R_2$, which define the transmission channel $TC_2$ including the ambient fluid itself, within a perforated housing such as to provide protection to those elements while at the same time exposing them for direct contact with the ambient fluid. In addition, sensor assembly 50 could be mounted on or integrally formed in another part of the processing chamber, e.g., the table holding the workpieces, or housed within a separate unit for manual introduction and removal as and where desired for making the respective measurements. Further, the sensor assembly may be used in other processing operations, e.g., heat treatment of parts.

Many other variations, modifications and applications of the invention will be apparent.

What is claimed is:

1. A sensor system immersible in an ambient fluid for sensing at least two conditions of the ambient fluid, comprising:
    a sealed chamber filled with a reference fluid of a know composition and/or pressure;
    a first energy wave transmission channel defined by a first transmitter at one end of the transmission channel, a first receiver at the opposite end of the transmission channel, and said reference fluid in between;
    a second energy wave transmission channel defined by a second transmitter at one end, a second receiver at the opposite end, and said ambient fluid inbetween;
    and measuring circuitry for measuring:
        (a) the transit time of an energy wave through said first transmission channel, and for utilizing the latter measurement to determine the temperature of the fluid within said sealed chamber, and thereby the temperature of said ambient fluid in which the sensor system is immersed; and
        (b) the transit time of an energy wave through said second transmission channel, and for utilizing the latter measurement to determine the composition and/or the pressure of said ambient fluid in which the sensor system is immersed; wherein said first and second energy wave transmission channels are carried by a common housing to be enveloped by the ambient fluid.

2. The sensor system according to claim 1, wherein said common housing includes walls defining said sealed chamber containing said reference fluid, said first transmitter, and said first receiver defining said first energy wave transmission channel;
    an outer surface of said walls being exposed to said ambient fluid and carrying said second transmitter and second receiver defining said second energy wave transmission channel with said ambient fluid inbetween.

3. The sensor system according to claim 2, wherein said walls defining said sealed chamber are rigid, and the reference fluid therein is of a known composition to enable the temperature and composition of the ambient fluid to be determined.

4. The sensor system according to claim 2, wherein at least one wall defining said sealed chamber is pressure-deformable, and the reference fluid therein is initially of a known pressure to enable the temperature and pressure of the ambient fluid to be determined.

5. The sensor system according to claim 1, wherein said reference fluid is a gas.

6. the sensor system according to claim 1, wherein said reference fluid is water of a known pH, to enable the sensor system to be used for measuring the temperature and pH of a body of water.

7. The sensor system according to claim 1, wherein said energy wave is a sonic wave.

8. The sensor system according to claim 1, wherein said sensor system further comprises:
    a second sealed chamber filled with a second reference fluid of a known composition and/or pressure;
    said second sealed chamber including a third transmitter and a third receiver defining a third energy wave transmission channel with said second reference fluid therein;
    said measuring circuitry also measuring:
        a. the transit time of an energy wave through said third energy wave transmission channel and utilizing the latter measurement to determine the composition and/or the pressure of said ambient fluid.

9. The sensor system according to claim 8, wherein the first-mentioned sealed chamber is defined by rigid walls such that measuring the transit time of an energy wave through said first energy wave transmission channel enables the sensor system to determine the temperature and composition of the ambient fluid;
    and wherein said second sealed chamber is defined by at least one wall which is pressure-deformable, the reference fluid within said second sealed chamber being initially of a known pressure such that measuring the transit time of an energy wave through said third energy wave transmission channel also enables the sensor system to determine the pressure of said ambient fluid.

10. The sensor system according to claim 8, wherein said first, second and third energy wave transmission channels are all carried by a common housing to be enveloped by said ambient fluid.

11. The sensor system according to claim 10, wherein said common housing includes rigid walls defining said first-mentioned sealed chamber such that measuring the transit time of an energy wave through said first energy wave transmission channel enables the sensor system to determine the temperature and composition of the ambient fluid;
    and wherein said common housing includes further walls, at least one of which is pressure-deformable, defining said second sealed chamber, the reference fluid within said second sealed chamber being initially of a known pressure such that measuring the transit time of an energy wave through said third energy wave transmission channel also enables the pressure of said ambient fluid to be determined.

12. The sensor system according to claim 11, wherein said transmitter and receiver exposed to said ambient fluid are located on one side of said first-mentioned sealed chamber, and said second sealed chamber is located on another side of said first-mentioned sealed chamber.

13. The sensor system according to claim 8, wherein said first and second reference fluids are gases of known composition and/or pressure.

14. The sensor system according to claim 8, wherein said first and second reference fluids are liquids.

15. The sensor system according to claim 9, wherein said energy wave is a sonic wave.

16. A processing device for processing workpieces comprising a sensor system according to claim 1 included within said chamber.

17. The processing device for according to claim 16, wherein said sensor system is integrally formed in a wall or other structure of said chamber.

18. The processing device according to claim 16, wherein said chamber further includes an electrical heater for heating the interior of the chamber, a source of gases for introduction into said chamber, and a controller for automatically controlling said electrical heater in response to the measured temperature to maintain a desired temperature within the interior of the chamber, and for automatically controlling said source of gases to maintain a desired mixture composition in the interior of said chamber.

19. The processing device according to claim 16, wherein said chamber further includes a supporting structure for supporting a workpiece therein, said supporting structure including a further transmitter and a further receive defining a further transmission channel through a portion of the workpiece for measuring the actual temperature of the workpiece.

* * * * *